(12) United States Patent
Ben Gad et al.

(10) Patent No.: US 11,610,684 B2
(45) Date of Patent: Mar. 21, 2023

(54) AUTOMATED SYSTEM AND METHOD FOR EVALUATION AND REPORT OF PASSENGER PAIN AND TRAUMA IN A VEHICULAR CRASH

(71) Applicant: MDGo Ltd., Haifa (IL)

(72) Inventors: Itay Ben Gad, Jerusalem (IL); Gilad Avrashi, Haifa (IL); Eli Zerah, Kiryat Ata (IL); Amit Kerterman, Nazareth Illit (IL)

(73) Assignee: MDGO LTD., Haifa (IL)

( * ) Notice: Subject to any disclaimer, the term of this patent is extended or adjusted under 35 U.S.C. 154(b) by 488 days.

(21) Appl. No.: 16/809,444

(22) Filed: Mar. 4, 2020

(65) Prior Publication Data
US 2020/0273582 A1 Aug. 27, 2020

Related U.S. Application Data

(63) Continuation-in-part of application No. PCT/IL2018/050986, filed on Sep. 5, 2018.
(Continued)

(51) Int. Cl.
*G08B 23/00* (2006.01)
*G16H 50/30* (2018.01)
(Continued)

(52) U.S. Cl.
CPC ........... *G16H 50/30* (2018.01); *A61B 5/4824* (2013.01); *A61B 5/6893* (2013.01);
(Continued)

(58) Field of Classification Search
CPC ........ G16H 50/30; G16H 10/60; G16H 15/00; G16H 40/67; G16H 50/20; G16H 40/63; G16H 50/50; G16H 80/00; A61B 5/4824; A61B 5/6893; A61B 5/7267; A61B 5/747; A61B 2562/0247; B60R 21/01508; B60R 21/01516; B60R 21/01544; G06Q 50/04;
(Continued)

(56) References Cited

U.S. PATENT DOCUMENTS 9,108,582 B1 8/2015 Kozloski et al.
9,886,841 B1 2/2018 Nave et al.
(Continued)

FOREIGN PATENT DOCUMENTS

JP 2015-207049 A 11/2015
WO 2014207558 A2 12/2014
WO 2017082756 A1 5/2017

OTHER PUBLICATIONS

European Search Report from European Application No. 20736153.6, dated Sep. 5, 2022; 9 pgs.
(Continued)

*Primary Examiner* — Anh V La
(74) *Attorney, Agent, or Firm* — Polsinelli PC

(57) ABSTRACT

A system and method for evaluating and reporting of trauma to organs of passengers in a vehicular crash in real time is provided. The systems and methods include and use one or more in-vehicle sensors, a processor, a server, and one or more non-transitory computer-readable media to analyze a crash and trauma to passengers. The systems and methods may be further configured to optimize operation of a vehicle to minimize trauma.

24 Claims, 9 Drawing Sheets

Related U.S. Application Data

(60) Provisional application No. 62/690,973, filed on Jun. 28, 2018, provisional application No. 62/554,030, filed on Sep. 5, 2017.

(51) Int. Cl.
| | |
|---|---|
| *B60R 21/015* | (2006.01) |
| *G16H 40/67* | (2018.01) |
| *G16H 10/60* | (2018.01) |
| *G16H 15/00* | (2018.01) |
| *G16H 50/20* | (2018.01) |
| *A61B 5/00* | (2006.01) |
| *G06Q 50/04* | (2012.01) |
| *G06Q 50/26* | (2012.01) |
| *G07C 5/08* | (2006.01) |
| *G07C 5/00* | (2006.01) |

(52) U.S. Cl.
CPC ............ *A61B 5/7267* (2013.01); *A61B 5/747* (2013.01); *B60R 21/01508* (2014.10); *B60R 21/01516* (2014.10); *B60R 21/01544* (2014.10); *G06Q 50/04* (2013.01); *G06Q 50/265* (2013.01); *G07C 5/008* (2013.01); *G07C 5/0808* (2013.01); *G07C 5/0841* (2013.01); *G16H 10/60* (2018.01); *G16H 15/00* (2018.01); *G16H 40/67* (2018.01); *G16H 50/20* (2018.01); *A61B 2562/0247* (2013.01)

(58) Field of Classification Search
CPC .... G06Q 50/265; G07C 5/008; G07C 5/0808; G07C 5/0841; G07C 5/08; G08B 25/08; H04W 4/44
USPC .......... 600/587; 340/573.1, 575, 576, 539.13
See application file for complete search history.

(56) References Cited

U.S. PATENT DOCUMENTS

| | | | |
|---|---|---|---|
| 10,360,601 B1 * | 7/2019 | Adegan | G06Q 30/0283 |
| 2002/0103622 A1 * | 8/2002 | Burge | G16Z 99/00 |
| | | | 702/183 |
| 2008/0136613 A1 * | 6/2008 | Takafuji | B60R 21/0132 |
| | | | 340/436 |
| 2008/0208814 A1 | 8/2008 | Friedlander et al. | |
| 2012/0109241 A1 * | 5/2012 | Rauscher | A61N 1/326 |
| | | | 607/45 |
| 2015/0232090 A1 * | 8/2015 | Jeon | B60W 50/14 |
| | | | 701/1 |
| 2016/0094964 A1 | 3/2016 | Barfield, Jr. et al. | |
| 2016/0292759 A1 * | 10/2016 | Gonzalez Miranda | |
| | | | G06F 3/04845 |
| 2017/0067750 A1 * | 3/2017 | Day | G08G 1/096716 |

OTHER PUBLICATIONS

European Search Report for corresponding EP Application No. 18852936.6 (10 pages).

* cited by examiner

AUTOMATED SYSTEM AND METHOD FOR EVALUATION AND REPORT OF PASSENGER PAIN AND TRAUMA IN A VEHICULAR CRASH

The present Application is a Continuation-in part of international PCT application No. PCT/IL2018/050986 that claims the priority dates of two US provisional applications: 62/554,030, filed 5 Sep. 2017; and 62/690,973, filed 28 Jun. 2018; each of the foregoing documents are incorporated in their entireties herein by reference.

FIELD OF THE INVENTION

The invention is in the field of vehicle telematics systems, and in particular to those employed to report injuries of passengers in a vehicular crash.

BACKGROUND TO THE INVENTION

According to the Association for Safe International Road Travel (ASIRT), nearly 1.3 million people worldwide die in road crashes each year and an additional 20-50 million are injured or disabled. Well-established cadres of emergency personnel—including emergency medical teams (EMTs), trauma units, and hospital emergency departments—are on continuous alert, ready to treat victims of car crashes.

In recent years there have been efforts to employ automotive sensor, computer, and communication technologies to prepare emergency personnel for treatment of passengers involved in vehicular accidents, with information about the type of accident and possible injuries sustained by the passengers.

US2002103622A discloses a decision-aid system that receives, analyzes, manages and communicates data from vehicle crash sensors for use by trauma system personnel in treating injured occupants from the vehicles which produced the crash sensor data. The system utilizes a computer system that accepts and analyzes vehicle crash data from vehicle communication systems connected to crash sensors that generate data when a vehicle is involved in a crash. Crash sensor data is stored on a central network for remote access by trauma system personnel and others providing response services and medical services to injured vehicle occupants. By gaining access to crash sensor data, analyzed crash sensor data and other information, accurate patient transport, handling and treatment decisions can be made.

A study, "Development and Validation of the URGENCY Algorithm to Predict Compelling Injuries" (*J. Proc. Int. Tech. Conf. Enhanced Safety Vehicles*, J. Augenstein et al., 2001), discloses an algorithm using data from on-board crash recorders to assist in identifying crashes that are most likely to have time critical (compelling) injuries. Logistic regression with weighing factors was applied to published crash data, in order to estimate coefficients of known predictor variables, used in a formula to calculate the probability of a casualty.

U.S. Pat. No. 9,886,841B discloses a system for notifying emergency services of a vehicular crash that may (i) receive sensor data of a vehicular crash from at least one mobile device associated with a user; (ii) generate a scenario model of the vehicular crash based upon the received sensor data; (iii) store the scenario model; and/or (iv) transmit a message to one or more emergency services based upon the scenario model. As a result, the speed and accuracy of deploying emergency services to the vehicular crash location is increased. The system may also utilize vehicle occupant positional data, and internal and external sensor data to detect potential imminent vehicle collisions, take corrective actions, automatically engage autonomous or semi-autonomous vehicle features, and/or generate virtual reconstructions of the vehicle collision.

SUMMARY

The present invention relates to a system and method for evaluating and reporting trauma suffered by organs of one or more passengers in a vehicular crash to an emergency management client, automatically and in real time, wherein the emergency management client comprises or is in communicative connection with computer(s) of one or more medical care providers selected from (but not limited to) an EMS unit, a trauma unit, an emergency room and any other medical care unit. An aspect of the invention relates to steps for improving accuracy of an algorithm for trauma report accuracy, by optimization or training, as the system receives feedback comprising an aggregation of medical examination reports, from medical treatment providers, of injured passengers processed by the system.

In a specific embodiment, the method comprises steps of 1) taking readings of in-vehicle sensors during a car accident; 2) wirelessly transmitting the readings to a server; 3) classifying a type of crash (head-on, side impact, etc.); 4) computing forces exerted on an organ of a passenger in the vehicle; 5) assessing trauma to the organ, based on the forces and published medical data; 6) generating a pain model based on the forces; and/or 7) sending a trauma assessment report, which can include the pain model to a medical emergency client. The trauma assessment report can vastly hasten and improve response of medical care providers, such as EMS, trauma units, and emergency-room personnel to properly prepare for the accident and treat the injured passenger. The method further comprises steps of 8) receiving a medical examination report of injuries sustained by the passenger, An aggregation of such medical examination reports, acquired over a number of accidents, can be used for training in order to improve trauma assessment accuracy of the method.

In a further specific embodiment, the server of the system comprises a kinetics engine and a trauma analysis engine. The kinetics engine calculates applied forces and motions of a passenger in a vehicular accident. In some embodiments, the kinetics engine calculates forces and motions measured by "virtual sensors," imaginary sensors disposed inside organs of the passenger; readings of a virtual sensor is computed as a function of the position of the virtual sensor, the crash type, and the in-vehicle sensor readings. The trauma analysis engine estimates trauma to the organs, based on forces to organs calculated by the kinetics engine. The pain model can be generated by analysis of the forces applied to the occupant including, but not limited to, muscles, joints, organs, bones and/or combinations thereof, to estimate a pain level. In some instances, the pain model can categorize a pain level corresponding to symptoms and/or symptom intensity.

Dividing the calculation into two analyses of the passenger, kinetic, pain and trauma assessment, allows the system to tap into a wealth of published data for training the system: for training the kinetics engine, data of crash tests with dummies and simulation results; for the pain model and the trauma analysis engine, medical literature on trauma to organs.

The present invention provides an automated system for evaluating and reporting of pain of passengers in a vehicular crash in real time, comprising
  a. one or more in-vehicle sensors, configured to take readings during a crash of a vehicle;
  b. an in-vehicle processor, configured to receive the readings from the in-vehicle sensors;
  c. a server in wireless communicative connection with the in-vehicle processor, the server comprising one or more processors and non-transitory computer-readable media (CRM);
  d. one or more emergency management clients;
  e. the CRM storing a database of medical literature;
  f. the server further comprising a kinetics analysis engine configured to
    i. receive the sensor readings from the in-vehicle processor;
    ii. classify a crash mechanism of the vehicular crash, as a first function of first inputs comprising the in-vehicle sensor readings;
    iii. calculate readings of virtual sensors, virtually disposed inside one or more organs of a passenger in the vehicle; the readings of virtual sensors calculated as a second function of second inputs comprising the classified crash mechanism and the in-vehicle sensor readings;
  g. the server further comprising a trauma analysis engine configured to
    i. receive the virtual sensor readings from the kinetics analysis engine;
    ii. assess trauma to the organs, as a third function of third inputs comprising the virtual sensor readings and the medical literature in the medical literature database;
    iii. generate a pain model corresponding to the readings of the virtual sensors and/or the trauma to the organs; and
    iv. send a trauma assessment report, comprising the pain model, and the estimated organ trauma, to the emergency management clients;
wherein the system further comprises a medical information client and a system history database; and
  h. the server is further configured to receive a medical examination report of a post-accident examination of the passenger from the medical information client and to store the medical examination report and the associated virtual sensors readings in the system history database; and
  i. the server further comprises a third optimization engine configured to employ one or more optimization techniques, to optimize the third function against an aggregation of the medical examination reports and the associated readings of the virtual sensors stored in the system history database.

The present invention further provides a method for evaluating and reporting of trauma to organs of passengers in a vehicular crash in real time, comprising steps of
  a. providing the abovementioned system;
  b. receiving sensor readings taken during a crash of a vehicle;
  c. receiving data of the sensor readings by a server;
  d. classifying a crash mechanism of the crash, as a first function of first inputs comprising the sensor readings;
  e. calculating readings of virtual sensors, virtually disposed inside one or more organs of a passenger in the vehicle, as a second function of second inputs comprising the classified crash mechanism and the in-vehicle sensor readings;
  f. assessing trauma to the organs, as a third function of third inputs comprising the virtual sensor readings and medical literature;
  g. generating a pain model corresponding to the readings of the virtual sensors and/or the trauma to the organs;
  h. sending a trauma assessment report, comprising the pain model and the estimated organ trauma, to one or more emergency management clients;
wherein method further comprises steps of
  i. receiving a medical examination report of a post-accident examination of the passenger; and
  j. employing one or more optimization techniques to optimize the third function against an aggregation of the received medical examination reports and associated readings of the virtual sensors.

The present invention further provides the abovementioned system or method, wherein the in-vehicle sensors and the in-vehicle processor are provided in a new vehicle by a supplier/manufacturer of the vehicle.

The present invention provides any of the abovementioned systems or methods, wherein the sensors are in a group comprising OEM sensors, aftermarket sensors, and any combination thereof.

It is further provided by the present invention, any of the abovementioned systems or methods, wherein the one or more in-vehicle sensors are selected from a group comprising a linear accelerometer, a speedometer, three-axis accelerometer, microphone, inside air temperature sensor, outside air temperature sensor, seat occupancy sensor, seat position sensor, safety belt use indicator, safety belt tension meter, airbag deployment sensor, wheel speed sensor, blind-spot monitor, throttle position sensor, braking force sensor, steering wheel position sensor, steering angle sensor, hands-on-steering wheel sensor, tire air pressure sensor, optical sensor, rear view monitor, in-cabin camera, air pressure sensor, acoustic sensor, ultrasound sensor, LiDAR, RADAR, GPS, gyroscopic sensor, tachometer, passenger height sensor, passenger weight sensor, and any combination thereof.

It is further provided by the present invention, any of the abovementioned systems or methods, wherein the in-vehicle sensors further comprise sensors configured for direct measurement of force on organs of the passenger, the sensors comprising one or more of
  a. one or more pressure sensors, each disposed at a top, bottom, or buckle of a seatbelt of the vehicle;
  b. a pressure sensor disposed on a headrest of the vehicle, optionally with a gyroscope configured to measure acceleration of the headrest;
  c. one or more pressure sensors disposed on a back of a steering wheel of the vehicle;
  d. one or more pressure sensors, each disposed on a seat, seat back, or inflated airbag zones of the vehicle.

It is further provided by the present invention, any of the abovementioned systems or methods, wherein the in-vehicle sensors further comprise a plurality of sensors detecting distances between themselves, the sensors disposed in different parts of the vehicle and the kinetics engine further configured for calculation of deformation of the vehicle in the crash.

The present invention further provides any of the abovementioned systems or methods, wherein the in-vehicle processor is further configured to compress data of the sensor readings.

The present invention further provides any of the abovementioned systems or methods, wherein the server is in a group comprising a cloud server, a dedicated server, and any combination thereof.

In a further embodiment, the present invention provides any of the abovementioned systems or methods, wherein the classification of a crash mechanism is from a group comprising rear impact, side impact, rollover and frontal impact collisions, and any combination thereof.

In accordance with a further embodiment the present invention provides any of the abovementioned systems or methods, wherein the second function employs one or more data-science algorithms.

The present invention further provides any of the abovementioned systems or methods, wherein the virtual sensors are configured to measure one or more of a group comprising force, linear acceleration, moments of inertia, angular acceleration, angular velocity, stress, and displacement of one or more parts of the human body during acceleration (including deceleration) resulting from the crash.

The present invention further provides any of the abovementioned systems or methods, further comprising a sub-system for training of a response function for the virtual sensors and, optionally, a response function for the classification; the sub-system comprising a crash scenario database, a sensor simulator, a test crash data client, and a second optimization engine, and, optionally, a first optimization engine, wherein
   a. the crash scenario database is configured to provide parameters of a crash scenario;
   b. the sensor simulator is configured to receive the crash scenario and to compute simulated sensor responses of the in-vehicle sensors for the scenario;
   c. the kinetics engine is further configured to receive the simulated sensor responses and compute simulated virtual sensor readings as the second function (and, optionally, a simulated classification as the first function) of the simulated sensor responses;
   d. the test crash data client is configured to provide test-car data and test-dummy data from a crash test performed under conditions of the crash scenario; and
   e. the second optimization engine (and optional first optimization engine) is configured to
      i. receive simulation data comprising the crash scenario, the simulated sensor responses, the simulated virtual sensor readings (and optionally, the simulated classification), the test-car data, and the test-dummy data;
      ii. store the simulation data in the system history DB;
      iii. optimize the second function and, optionally, the first function, against an aggregation of one or more instances of the simulation data stored in the system history DB.

In accordance with a further embodiment, the present invention provides any of the abovementioned systems or methods, wherein the optimization techniques for the one or more of the function are selected from a group comprising random forests, linear regression, logistic regression, k-nearest neighbors, gradient boost, recurrent neural network, long-short term memory, gated recurrent unit, generative adversarial network, machine learning, deep learning, and any combination thereof.

The present invention provides any of the abovementioned systems or methods, wherein the third function is further a function of outputs from one or more of the in-vehicle sensors.

The present invention provides any of the abovementioned systems or methods, wherein the system further comprises wellness monitoring sensors and the third inputs to the third function further comprise outputs from the wellness monitoring sensors for making the assessment report of trauma to organs, wherein the wellness monitors are selected from a group comprising a heart rate monitor, blood pressure monitor, dehydration monitor, glucometer, skin moisture, pupil diameter monitor, eyelid opening height monitor, breathing monitor, posture monitor, and any combination thereof.

The present invention further provides any of the abovementioned systems or methods, wherein the third function further employs one or more deterministic models in a group comprising biomechanical models, finite elements, and 3D models.

Furthermore the present invention provides any of the abovementioned systems or methods, wherein the trauma analysis engine is further configured to dynamically increase reliance on the optimization of the third function over the deterministic models, with a growth in number of the aggregation of the medical examination reports and the associated virtual sensor readings stored in the system history database.

The present invention further provides any of the abovementioned systems or methods, wherein the medical examination report comprises standard medical criteria selected from any in a group comprising head injury, AIS, ICD-9, ICD-10, and any combination thereof.

In a further embodiment the invention provides any of the abovementioned systems or methods, wherein the medical examination report is entered in a user interface provided by an application installed in the medical information client.

The present invention further provides any of the abovementioned systems or methods, wherein the third function is further configured to:
   a. calculate forces to one or more tissues in a group comprising pelvis, RLQ, LLQ, RUQ, LUQ, femur, chest, head, spine;
   b. employ a reverse engineered human body model—selected from a group comprising MADYMO, GHBMC, THUMS, and any combination thereof—to calculate approximate movement of the body during the crash; and
   c. employ a finite elements model to calculate the damage to one or more organs.

The present invention provides any of the abovementioned systems or methods, wherein the third function comprises a dedicated calculation algorithm for each of the organs.

The present invention further provides any of the abovementioned systems or methods, further comprising a passenger information database.

In yet a further embodiment the present invention provides any of the abovementioned systems or methods, wherein the second function is configured to apply a dedicated calculation algorithm to a specific condition of one of the organs of the passenger stored in the passenger information database.

The present invention provides any of the abovementioned systems or methods, wherein the dedicated calculation algorithm is for a bone-tissue organ depending on the condition of the bone-tissue organ of the passenger, stored in the passenger information database, being normal, osteoporotic, or osteopetrotic.

Further provided by the present invention are any of the abovementioned systems or methods, wherein the third function is configured to calculate a probability of liver lacerations to the passenger due to fibrotic tissue, as a function of a history of liver cirrhosis stored in the passenger information database.

The present invention provides any of the abovementioned systems or methods, wherein the medical examination report is added to the passenger information database.

In yet a further embodiment of the invention, there is provided any of the abovementioned systems or methods, wherein the system is further configured for the passenger information database to store data from medical sensors monitoring the passenger.

In a further embodiment, the present invention provides any of the abovementioned systems or methods, wherein the trauma analysis engine is further configured to predict the probability that the passengers are trapped in the vehicle.

In further embodiments, the present invention provides any of the above systems or methods, wherein the pain model can categorize the pain level. The pain level can include symptomatic representation levels including, but not limited to, normal dynamic range, representative range of minimal to maximal pain prior to physical injury, range of actual structure damage (e.g soft tissue damage and/or bone damage).

The present invention provides any of the abovementioned systems or methods, wherein the trauma analysis engine is further configured to determine one or more appropriate trauma units needed to attend to the passengers.

The present invention further provides any of the abovementioned systems or methods, wherein the trauma unit determination is made as a function of one or more in a group comprising distance of the trauma unit from the crash, the trauma units' availability, equipment, and medical knowledge.

The present invention further provides any of the abovementioned systems or methods, wherein the report is sent to the client computer using a technology selected from Webpush, HTTP server push, Pushlet, long polling, Flash XML-Socket relays, Reliable Group Data Delivery, push notification, Javascript, and any combination thereof.

The present invention further provides any of the abovementioned systems or methods, further comprising an automotive manufacturing client configured to receive data collected in the system history data base.

The present invention provides any of the abovementioned systems or methods, wherein the server and the automotive client are further configured to compute an optimal braking and steering pattern before and during the crash of the vehicle that would result in minimizing severity of injuries, the optimization computed against an aggregation of the medical examination reports paired with associated measurements of the in-vehicle sensors.

The present invention further provides any of the abovementioned systems or methods, wherein the aggregation of medical examination reports and in-vehicle sensor measurements are from vehicles of the same type as the vehicle.

The present invention provides any of the abovementioned systems or methods, further comprising a marketing client, wherein the marketing client is configured to
 a. receive the trauma report;
 b. match the estimated organ trauma of the passenger to promoted medical products associated to the organ trauma;
 c. initiate a display of an advertisement on a device of the passenger for the matched medical products.

The present invention further provides any of the abovementioned systems or methods, wherein the system sends the trauma report to the marketing client upon confirming that the passenger was not immediately hospitalized after the crash.

DETAILED DESCRIPTION

Figure 1:
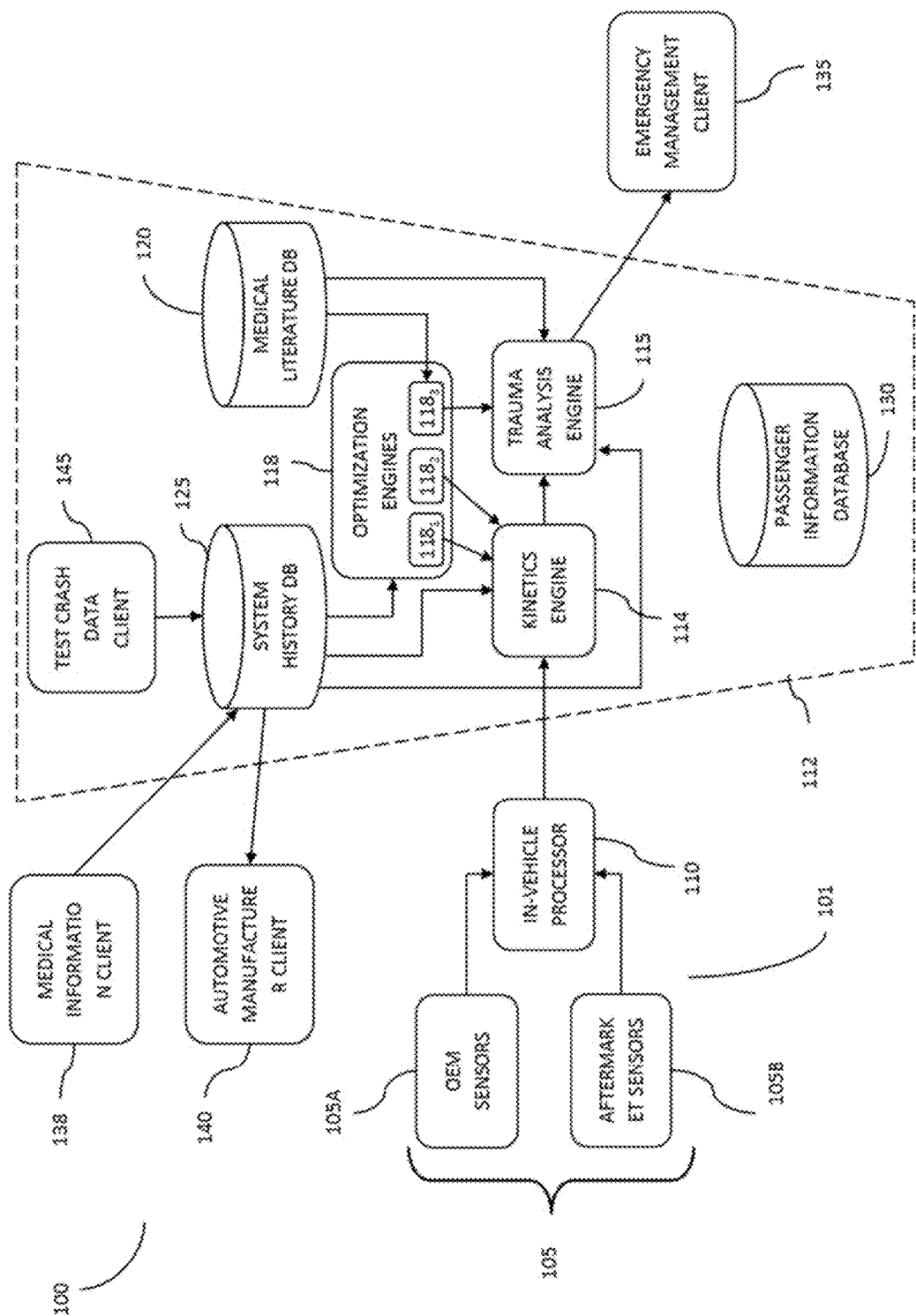
FIG. 1 shows a block diagram of a system for evaluating and reporting trauma to organs of passengers in a vehicular crash, according to some embodiments of the invention.

Reference is now made to FIG. 1, showing an automated system 100 for evaluating and reporting of trauma to organs of passengers in a vehicular crash in real time, according to some embodiments of the invention.

System 100 comprises in-vehicle sensors 105, an in-vehicle processor 110, a server 112 in wireless communication with in-vehicle processor 110, and client computers in communication with server 112, comprising an emergency management client 135 and a medical information client 138. Optionally, system 100 further comprises an auto-manufacturer client 140 in communication with server 112.

In-vehicle sensors 105 and in-vehicle processor 110 are disposed in a vehicle 101. In-vehicle sensors 105 and in-vehicle processor 110 can be OEM equipment provided by the manufacturer of vehicle 101, aftermarket equipment, or any combination thereof.

In-vehicle sensors 105 can include a speedometer, linear accelerometer, three-axis accelerometer, microphone, inside air temperature sensor, outside air temperature sensor, seat occupancy sensor, seat position sensor, safety belt use indicator, safety belt tension meter, airbag deployment sensor, wheel speed sensor, blind-spot monitor, throttle position sensor, braking force sensor, steering wheel position sensor, steering angle sensor, hands-on-steering wheel sensor, tire air pressure sensor, optical sensor, rear view monitor, in-cabin camera, air pressure sensor, acoustic sensor, ultrasound sensor, LiDAR, RADAR, GPS, gyroscopic sensor, tachometer, passenger height sensor, passenger weight sensor, and any combination thereof.

Reference is now made to FIGS. 2A-2D, showing several kinds of in-vehicle sensors 105, according to some embodiments of the invention. Illustrated in-vehicle sensors are distinguished in that they are disposed in contact or nearly in contact with a passenger, permitting measurement of external forces on organs of the passenger during an accident. It is understood that the in-vehicle sensors being shown in the figures and described below does not preclude embodiments of the invention in which one or more of these sensors is absent.

Figure 2A:
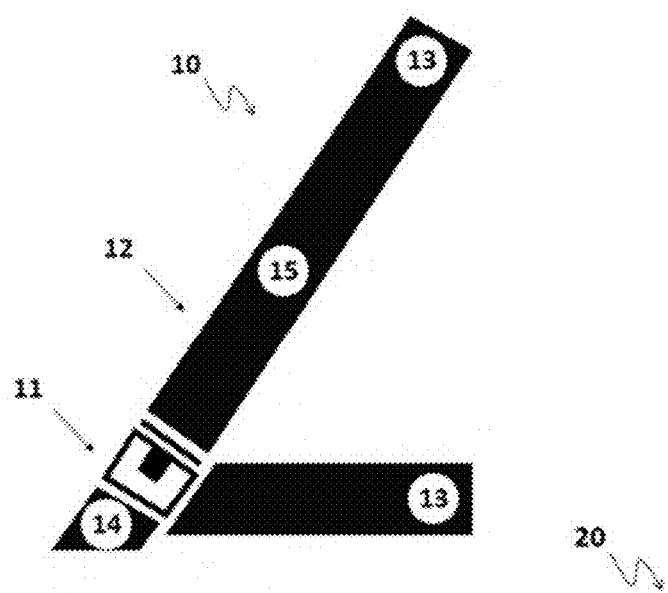
FIGS. 2A-2D show several kinds of in-vehicle sensors 105, according to some embodiments of the invention.

FIG. 2A shows an embodiment of a set of sensors located on a seatbelt 10 of the vehicle. Seatbelts are typically made of two parts: the buckle 11, which is usually a static element, and the belt 12 which is usually a dynamic element. In several embodiments of the present invention, pressure sensors 13 are allocated in the top and bottom parts of the belt 12, and another pressure sensor 14 is located at the buckle 11. Furthermore, a height-adaptable heartbeat and respiration sensor 15 is located on the belt 12. The passenger may change the position of this sensor to fit at the right place on the chest of the passenger.

Figure 2B:
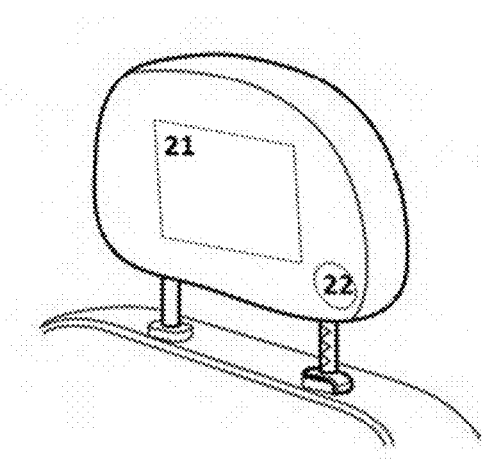

FIG. 2B shows sensors located on a headrest 20 of the vehicle. A pressure sensor 21 measures the pressure on the headrest 20 applied by the head of the passenger. Pressure sensor can 21 measure force typically applied to the head in a countercoup injury. Alternatively, or in addition, a gyroscope 22 measures the acceleration applied on the headrest 20 by the head of the user; furthermore, gyroscope 22 enables correlation of the movements of the head during an accident to those of the seat, by measuring the shear force applied by the seat on the body. Pressure sensor 21 and/or gyroscope 22 can enable measurement of forces sustained by the head in diffuse axonal injuries, measured by comparing the rotational head movement to the rotational force measured in the seat (back and bottom). Differences between those measurements will indicate shear force felt by the head and chest.

Figure 2C:
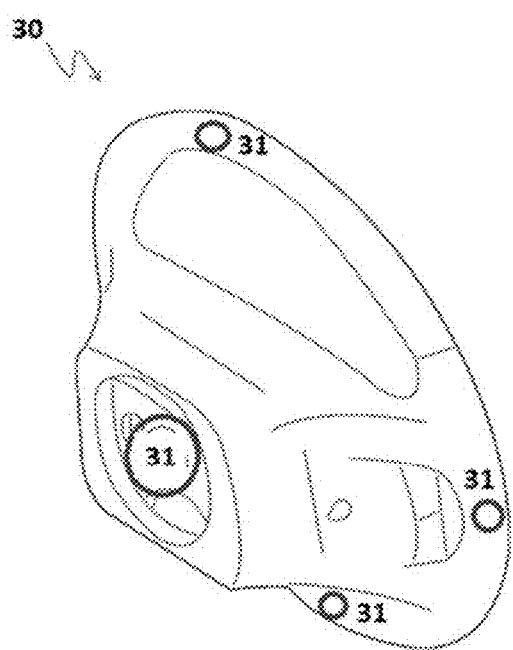

FIG. 2C shows a set of sensors located on the steering wheel 30 of the vehicle. Several pressure sensors 31 are located all around and on the back of the steering wheel 30. These sensors 31 provide information regarding the force of the impact of the passenger on the steering wheel 30, which can tell if the passenger had the seatbelt 10 on during the accident. This type of information is extremely important for the medical treatment of the impacted passenger.

Figure 2D:
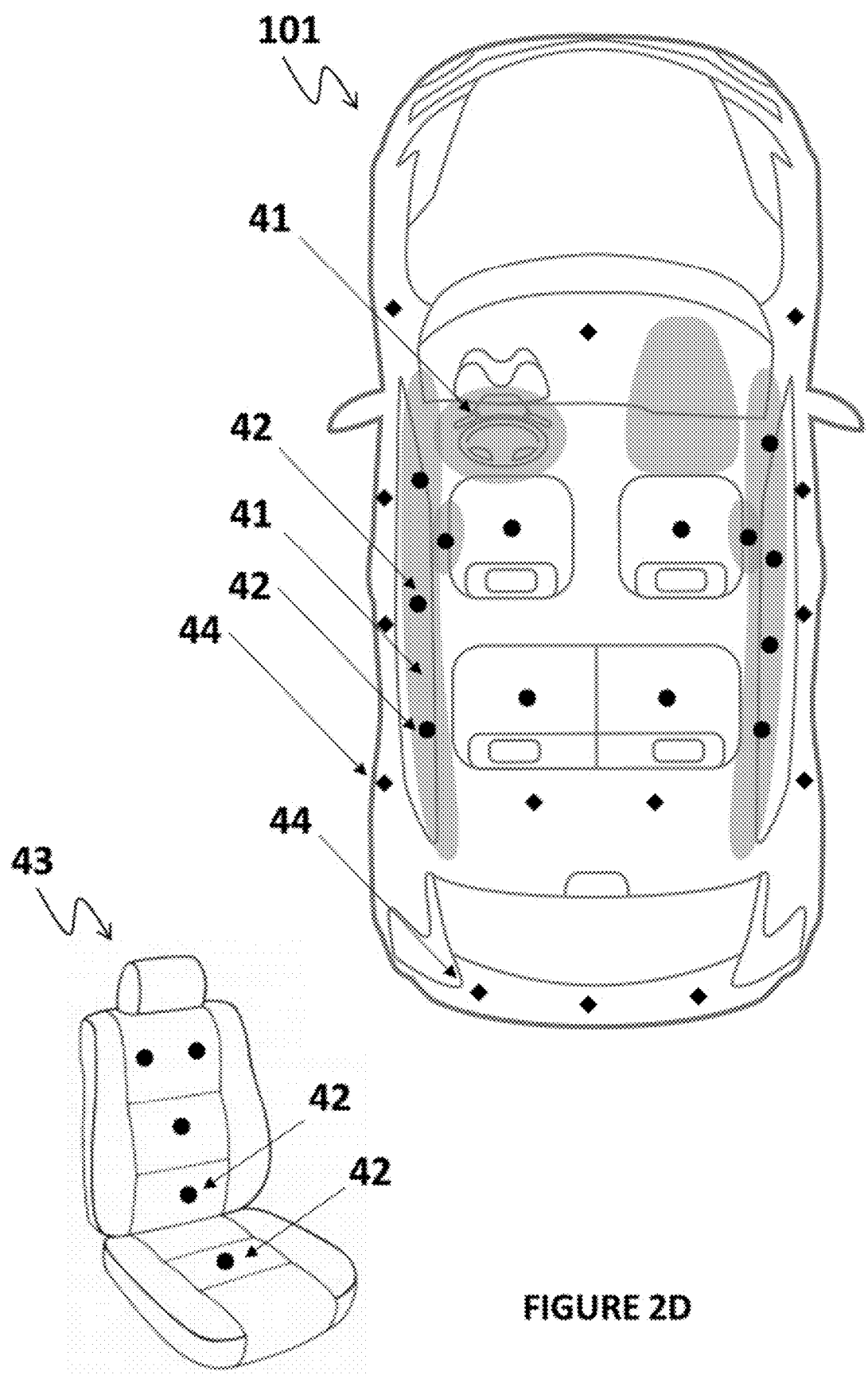
Figure 3:
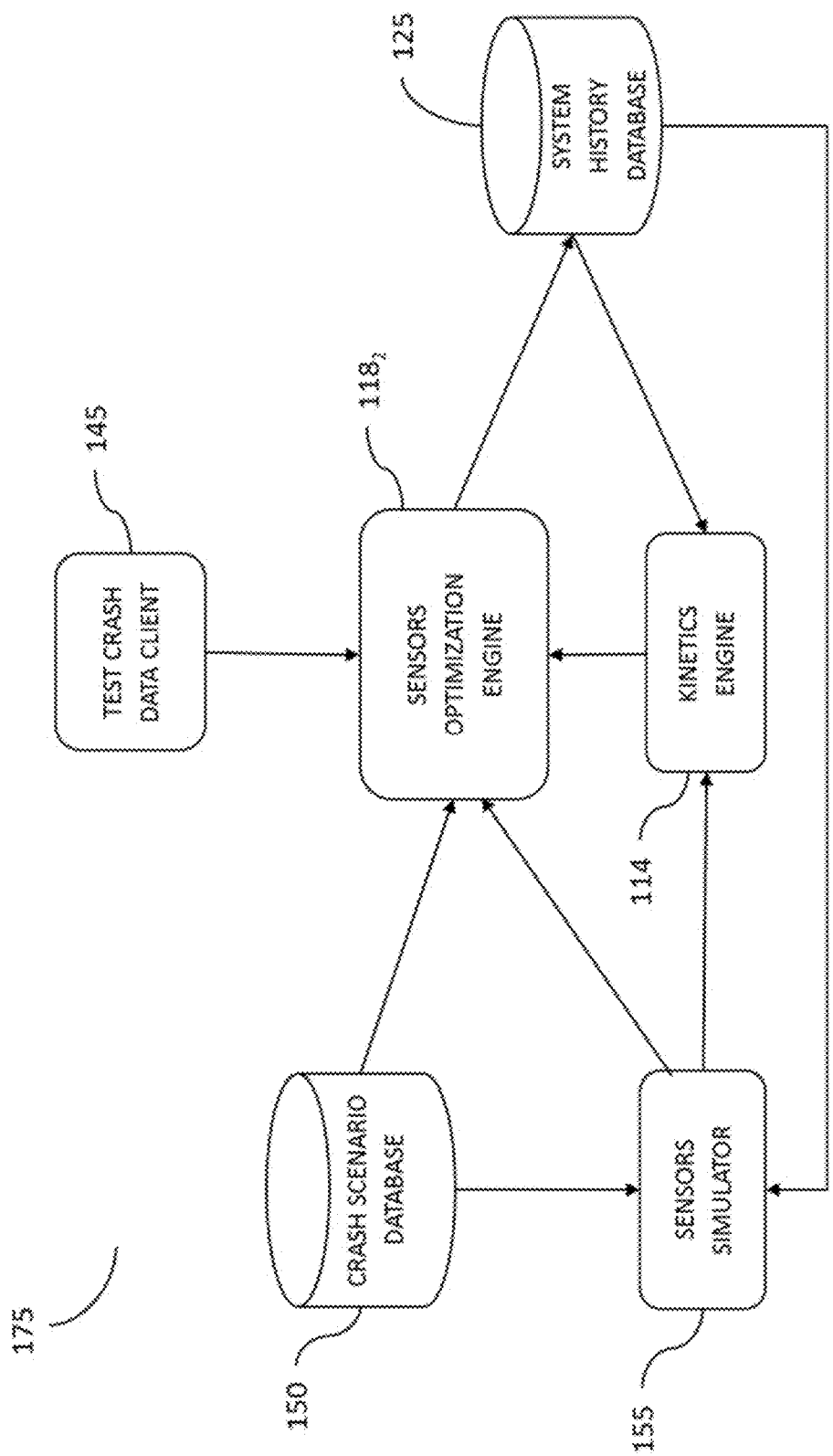
FIG. 3 shows a block diagram of a sub-system for training of response functions for classification and virtual sensors in a kinetic engine of a system for evaluating and reporting trauma to organs of passengers in a vehicular crash, according to some embodiments of the invention.

FIG. 2D shows of a set of sensors located in several places of the vehicle. A schematic view of vehicle 101 and a car seat 43 are shown, together with the zones (grey areas) of inflated airbags 41. Several pressure sensors (black dots) 42 are located at several places over the airbags and the seats. Pressure sensors 42, and other possible configurations of sensors, allow creating a fuller picture of the movements and impacts of passengers in order to achieve a fuller picture of their injuries.

In some embodiments, there are sensors 44 allocated in parts of vehicle 101 that can calculate the distance between themselves. This feature enables the calculation of deformations of vehicle 101 during the accident. It has been proven that there is a direct correlation between the level of deformation suffered by the vehicle and the severity of the injuries suffered by the passengers ("Characteristics of Crashes that Increase the Risk of Serious Injuries"; J. Augenstein, E. Perdeck, and J. Stratton; *Annual Proceedings of the Association for the Advancements of Automotive Medicine*; vol. 47, 2003). Therefore, as part of the overall sensorial information collected by the sensors, a level of deformation of the vehicle can be measured as another parameter for subsequent estimation of the extent of the injuries suffered by passengers in vehicle 101.

In some embodiments, in-vehicle sensors 105 include one or more medical sensors monitoring a passenger in the vehicle.

In-vehicle processor 110 receives readings of in-vehicle sensors 105. Upon detection that a crash has occurred, in-vehicle processor 110 sends data of readings received before and up to the time of the crash. In some embodiments, in-vehicle processor continues to receive and send data even after the vehicle comes to rest, in case there are multiple collisions. In preferred embodiments, in-vehicle processor 110 compresses the data before sending to server 112. An optimal compression may result in a loss of data, but a compression algorithm employed by in-vehicle processor is specially designed to preserve data features needed by server 112 for analysis of the crash.

In some embodiments, in-vehicle processor 110 may also collect information about passengers in the vehicle. At the start of a ride in vehicle 101, in-vehicle processor 110 may receive the passenger information—such as names, weights, heights, and medical conditions—at each seating location in vehicle 101, from a storage device (not shown) in vehicle, from an input device (not shown) in vehicle 101 or a mobile device, from server 112, or any combination thereof. A passenger may be identified by weight, height, and/or image, as measured by applicable in-vehicle sensors 105. The passenger information may be sent together with data from sensors 105, as additional input data to improve accuracy of estimating trauma to organs of the passengers. Additionally, passenger data may be stored in a passenger information database 130 (further described herein) of server 112.

Server 112 can be a cloud server or a dedicated server. Server 112 comprises one or more computers that can be disposed in different locations. Wireless communication between in-vehicle processor 110 and server 112 are be established with protocols suitable for vehicle-to-infrastructure or vehicle-to-cloud connectivity; e.g. one or more of cellular (such as 4G or 5G), IoT, etc.

Server 112 comprises modules (further described herein) that facilitate computations made by system 100. The modules comprise a non-transitory computer-readable medium (CRM), which can be any kind of memory or storage device, or combinations thereof. The CRM stores instructions for a processor of server 112 to execute the described functions of each module.

Clients, such as emergency management client 135 and medical information client 138, each comprise a computing device, which can be a PC, notebook, or mobile device such as a tablet or smartphone. Each computing device comprises a wired and/or wireless means of communication with server 112. On each client computer, a software agent may be installed, in order for the client computer to communicate with server 112 and otherwise provide functions of the client described herein.

Kinetics Analysis

In some embodiments, server 112 comprises a kinetics engine 114. Kinetics engine 114 receives the sensor readings sent by in-vehicle processor 110. Kinetics engine 114 classifies a crash mechanism of the crash from the sensor readings. For example, kinetics engine 114 determines whether the crash was a rear impact, side impact, or frontal impact collision. The classification identifies one of a discrete number of analysis regimes—e.g. readings of which in-vehicle sensors 105 to employ, which organs to analyze, which algorithm to use—for further processing by kinetics engine 114.

After classifying the crash, kinetics engine 114 calculates readings of virtual sensors. A virtual sensor is an imaginary sensor virtually disposed inside of an organ of a passenger in a vehicle. Virtual sensors convert physical quantities measured by in-vehicle sensors 105 into forces—which can include internal stresses—applied to the organ, resulting motions of the organ, and/or internal strain of the organ. In some embodiments, kinetics engine 114 employs various test data, data-science algorithms, and other computational methods (further described herein), as well as the crash mechanism classification, kinetics engine 114 calculates readings of virtual sensors in the body of a passenger as a function of readings from the in-vehicle sensors 105.

A virtual sensor may be a force/stress sensor or a displacement/deflection sensor, depending on what kinetic quantity is most important for evaluating life-threatening injuries. For impacts to the head, a virtual sensor typically measures stress at the center of gravity of the head. Virtual sensors placed in the chest typically measure internal deflections.

Kinetics engine 114 may determine body movements in order to help in calculating virtual sensor readings. For example, in a frontal crash 50 mph into a tree, the body is propelled toward the steering wheel with a specific velocity and an order of impact by body organs. If the chest hits the steering wheel first and the head second, the head will jerk forward and strains in the neck would result in a hyperflexion injury. If the head hits first, the head will be held back while the chest lurches forward, resulting in a hyperextension neck injury. A steering wheel adjustment sensor, passenger height sensor, seat sensors, and/or passenger height data in a passenger information database 130 (further described herein), for example, can be employed to determine which mode of impact occurred. The mode of impact can be, for example, an input to a calculation for a reading of a virtual sensor positioned in a vertebra of the neck.

Kinetics Optimization/Training

Reference is now made to FIG. 2, showing a sub-system 175 for optimizing/training the classification and virtual sensor response functions, of an automated system 100 for evaluating and reporting of trauma to organs of passengers in a vehicular crash in real time, according to some embodiments of the invention. Sub-system 175 comprises a crash scenario database 150, a sensors simulator 155, a kinetics engine 114, a system history database 125, a test crash data client 145, and a virtual sensor optimization engine $118_2$ (and/or a classification optimization engine $118_1$ for optimizing the classification function).

Crash scenario database 150 stores various test scenarios of car crashes; for example, car make/model, colliding body (e.g., other vehicle, concrete wall, tree, etc.), speed, braking/steering pattern, and passenger weight. Scenarios are strategically selected to minimize the number of test scenarios required to calibrate the virtual sensors. For example, at low vehicle speeds responses of some virtual sensors are expected to be nearly linear with respect to corresponding in-vehicle sensor readings, so a series of test scenarios at different vehicle speeds may be spaced by 10 mph (e.g., scenarios at 20, 30, and 40 mph). In the real-life system 100, virtual sensor responses at intermediate speeds can be calculated by interpolation of simulation data between the nearest lower and higher multiple of 10 mph. At higher speeds, virtual sensor responses may be non-linear, so that simulations and tests of crash scenarios at more closely spaced speeds, e.g. 50, 55, 60, 62, 64, 66, 68, 69, and 70 mph may be required.

Sensors simulator 155 receives a crash scenario from scenario database 150 and calculates expected responses of in-vehicle sensors 105 to a crash of the crash scenario, as a function of the crash scenario data. Such calculations are extremely computationally intensive; using present computer technology, sensors simulator 155 is typically left to run overnight to calculate the expected readings of in-vehicle sensors 105. A sensor simulation function may employ data-science algorithms. A sensor simulation function may employ existing training data of simulated sensor readings from one or more previous simulations by sensors simulator 155, stored in system history database 125. Sensors simulator 155 may combine results of data-science and trained algorithms with weighted emphasis; for example, a trained sensor simulator algorithm can become more relied upon when proven to be increasingly accurate with more training.

Kinetics engine 114 (further described herein) is run in a simulation mode when employed in optimization/training sub-system 175, wherein kinetics engine 114 receives the calculated sensor outputs from sensors simulator 155. Kinetics engine 114 computes simulated virtual sensor readings as a function of the simulated in-vehicle sensor readings. Typically, the simulated virtual sensor response function is identical to the virtual response function used by kinetics engine 114 in real crashes. A virtual sensor response function may employ data-science algorithms. A virtual sensor response function may employ existing training data of calculated readings of the virtual sensor from one or more previous simulations, stored in system history database 125. Kinetics engine 114 may combine results of data-science and trained algorithms with weighted emphasis; for example, a trained sensor simulator algorithm can become more relied upon when proven to be increasingly accurate with more training.

Test crash data client 145 provides data from sensors in crash dummies collected during actual crash tests. Test crash data client 145 can provide data from an automotive manufacturer, from a regulatory agency such as the U.S. National Highway Traffic Safety Administration (NHTSA), or from an insurance organization such as the Insurance Institute for Highway Safety (IIHS). Test crash data may be standard (tests required by law or regulations), non-standard, or both. Some test crashes can be performed specifically for the purpose of calibrating the classification and/or virtual sensor functions. In addition to sensors in the crash dummy—corresponding to virtual sensors of system 100—test crash data client 145 may also provide data for readings of in-vehicle sensors 105.

System history database 125 receives and stores data (or a reference link thereto) comprising the crash scenario from crash scenario database 150, corresponding simulated sensor outputs from sensors simulator 155, corresponding simulated virtual sensors readings from kinetics engine 114 and crash test data, performed under conditions of the crash scenario, from test crash data client 145.

Sensors optimization engine $118_2$ optimizes the sensor simulator function against an aggregation of one or more training sets (crash scenarios, sensor simulations, and in-vehicle sensor readings data from a crash test corresponding to the crash scenario) stored in system history database 125. Virtual sensors optimization engine $118_2$ stores parameters of the optimized in-vehicle sensor simulation function in the system history database.

Sensors optimization engine $118_2$ optimizes the virtual sensor response function against an aggregation of one or more training sets (crash scenarios, simulated virtual sensor readings, and readings of sensors in crash dummies from corresponding crash test data) stored in system history database 125. Virtual sensors optimization engine $118_2$ stores parameters of the optimized in-vehicle sensor simulation function in the system history database 125.

In some embodiments, sensors simulator 155 recomputes simulated sensor outputs with a newly optimized simulated sensor response function. Kinetics engine 114 receives the recomputed sensor outputs and computes revised virtual sensor readings, employing either the original virtual sensor response function or a newly optimized virtual sensor response function.

With more training, an aggregation of more and more simulations and corresponding test crash data is expected to improve accuracy of the sensor simulator and virtual sensor response functions. Optimization engines $118_1$-$118_2$ may employ one or more optimization methods, such as random forests, linear regression, logistic regression, k-nearest neighbors, gradient boost, recurrent neural network, long-short term memory, machine learning, deep learning, neural networks, fuzzy logic, and any combination thereof.

Trauma Assessment

Reference is now made again to FIG. 1. In some embodiments, server 112 further comprises a trauma analysis engine 115. Trauma analysis engine 115 receives virtual sensor readings from kinetics engine 114. Trauma analysis engine 115 assesses trauma to organs to a passenger in a vehicular crash, as a function of the virtual sensor readings and medical literature in a medical literature database 120 of server 112.

The trauma analysis may be done in two stages: 1) determining the effect of a force on a tissue's physical behavior. For this first stage, trauma analysis engine 115 may employ biomechanical models, finite elements, and 3D models; and 2) determining the effect of the tissue's physical behavior on the tissue damage and it's pathophysiology. For this second stage, trauma analysis engine may employ medical literature stored in the medical literature database 120. The medical literature comprises published medical literature (or links thereto); for example, medical journals such as *Traffic Injury Prevention* and/or medical references such as *Accidental Injury: Biomechanics and Prevention* (edited by N. Yoganandan, et al.).

Trauma analysis engine 115 calculates an assessment of trauma to the organs. Trauma analysis engine 115 identifies which organs of the passenger were traumatized and severity of the trauma. The calculation output can be based on codes of the Abbreviated Injury Scale (AIS) or of the International Classification of Diseases (ICD).

Based on the calculation of trauma analysis engine 115, server 112 sends a trauma assessment report to an emergency management client 135 of system 100. Emergency management client 135 is in connection with emergency medical personnel, such as an EMS unit, a hospital trauma unit, or hospital emergency room workers. Preferably, the trauma assessment report is push-reported to the personnel. Separate trauma assessment reports can be sent to trauma analysis engine 115 for each passenger in vehicle 101, categorized under the same vehicular accident. Trauma assessment can include the crash mechanism classification determined by kinetics engine 114. In some embodiments, trauma assessment reports are completely automatically generated.

Optionally, trauma analysis engine 114 can determine a most appropriate EMS and/or trauma unit to summon for treatment of the passenger(s). Server 112 can be further programmed to track the status of trauma units, and select which trauma unit to summon based on distance from the crash, availability, equipment, and medical knowledge of the trauma units.

Trauma assessment reports can be extremely valuable to EMS and hospital personnel preparing to respond to the accident and treat the passengers, as the reports apprise the personnel of types and severity of injuries and the number of passengers needing treatment. The report can quicken the speed of response and treatment, exceptionally critical for vehicular crashes. Furthermore, the report can include injuries that are often not detected by EMS and/or hospital personnel. Thus the report can summon medical personnel to an earlier intervention than otherwise possible.

For example, in many cases, when the abdomen is subjected to a blunt impact, solid and hollow organs are prone to major injuries. While solid-organ lacerations (liver, spleen) are visible in imaging (US, CT), injuries to hollow organs (e.g., bowel perforation) are usually undetectable. By analyzing the forces applied to the abdominal cavity, a rough estimation could be made in order to assess the potential damage.

Additionally, for example, in many cases of traumatic brain injury, a deterioration in Rotterdam score occurs during the first hours. Although the preliminary CT scan (usually taken during the first hour of treatment) seems unremarkable, by measuring the forces applied to the head during the impact, trauma analysis engine 114 can empirically assess a potential of deterioration, allowing the medical staff to respond accordingly and prevent the deterioration.

Server 112 may receive a response status from emergency management client 135. The status may include whether an ambulance was dispatched to the scene of the accident and at what time the ambulance arrived. The status may also include the time of an admission to an emergency room and to which hospital.

Figures 4A, 4B:
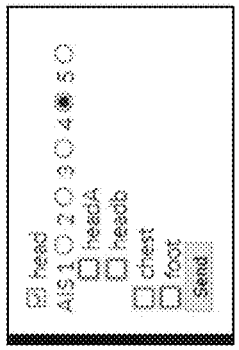
FIG. 4A shows a GUI of a medical examination report sent a server of a system for evaluating and reporting trauma to organs of passengers in a vehicular crash, according to some embodiments of the invention.
FIG. 4B shows a GUI of a status information screen of a system for evaluating and reporting trauma to organs of passengers in a vehicular crash, according to some embodiments of the invention.

System 100 further comprises a medical information client 138. Medical information client 138 provides medical examination reports prepared by EMS and/or hospital personnel during treatment (which can include emergency treatment, post-emergency inpatient treatment, outpatient treatment, and/or doctor visits) of passengers processed by system 100. Server 112 connects with medical information client 138. The format of the medical examination report can be specially prepared for use with system 100. FIG. 4A shows a GUI of a simplified example of a form for entering the medical examination report. A user of the form checks off organs that were injured in the accident. Under the organ appears selection buttons for reporting the extent of the injury on the AIS scale.

Server 112 receives medical examination reports of passengers in an accident processed by system 100. Server 112 stores the medical examination reports in system history database 125. FIG. 4B shows a status information screen visible to an administrator of server 112. The screen shows live and historical events (crashes), times of occurrence, crash mechanisms, extent of impact, response status, and links to medical examination reports.

In some embodiments, server 112 further comprises a trauma assessment optimization engine 118₃. Trauma assessment optimization engine 118₃ optimizes the trauma assessment function against an aggregation of one or more training sets comprising readings of virtual sensors and corresponding medical examination reports stored in system history database 125. Virtual sensors optimization engine 118$_2$ stores parameters of the optimized in-vehicle sensor simulation function in the system history database 125.

With more training, an aggregation of more and more virtual sensor readings and medical examination reports is expected to improve accuracy of the trauma assessment function. Trauma assessment optimization engine 1183 may employ one or more optimization methods, such as random forests, linear regression, logistic regression, k-nearest neighbors, gradient boost, recurrent neural network, long-short term memory, machine learning, deep learning, neural networks, fuzzy logic, and any combination thereof.

In some embodiments, trauma assessment optimization engine 1183 is further configured to dynamically increase reliance on the optimization over deterministic models (e.g., biomechanical models, finite elements, and 3D models), with a growth in number of the aggregation of medical examination reports and associated virtual sensor readings.

In some embodiments, server 112 further comprises a passenger information database 130 for one or more passengers in the vehicle. Kinetics engine 114 and/or trauma analysis engine 115 can employ data in passenger information database 130 to personalize analysis to a specific medical condition of a patient. For example, kinetics engine 114 can calculate kinetics of bone tissue, depending on whether the bone tissue is normal, osteoporotic, or osteopetrotic. For example, trauma analysis engine 115 can calculate a probability of liver lacerations due to fibrotic tissue, as a function of a history of liver cirrhosis.

An example is provided herein to demonstrate system operation:
- a. based on readings of in-vehicle seatbelt tension sensors taken during a crash, kinetics engine 114 determines that a 186G force was applied on the sternum of a passenger for 4 ms.
- b. trauma analysis engine 115, employing finite element analysis, determines that the sternum compressed posteriorly by 3 cm.
- c. based on age, gender, and medical history, trauma analysis engine 115 determines there is a 72% chance that passenger has a sternal fracture.

In some embodiments, system 100 further comprises an automotive manufacturer client 140. Automotive manufacturer client can connect to server 112. Automotive manufacturer client 140 can collect aggregated data of crashes processed by system 100. Automotive manufacturer client 140 can compute a braking and steering pattern before and during a crash that would result in minimizing severity of injuries, against an aggregation of medical examination reports paired with in-vehicle sensor readings, in particular sensors of the braking and steering system. An automotive manufacturer can deploy the optimized braking and steering patterns in designing a crash-response system of autonomous or semi-autonomous vehicles.

Alternatively, server 112 determines an optimal vehicle maneuver (e.g., location and orientation of the vehicle every millisecond prior to the crash), and then automotive client 140 calculates steering and braking required by vehicle 101 to achieve the optimal maneuver.

In some embodiments, system 100 further comprises a marketing client (not shown). The marketing client is connected to server 112. The marketing client can receive a trauma assessment report of a passenger from system history database 125. The marketing client can match the estimated organ trauma with promotional medical products associated with the estimated organ trauma. The marketing client can initiate a display of an advertisement for the products on a device of the passenger. In preferred embodiments, the marketing client withholds sending the promotion, or server 112 withholds access to the trauma assessment report, if the passenger was hospitalized for his injuries (e.g., if a medical examination report for the accident was generated by a hospital and is stored in system history database 125). In some embodiments, marketing client can withhold sending the promotion if the trauma exceeds a pre-defined threshold for the organ (as indicated in the trauma assessment or medical examination report).

Reference is now made to FIG. 4, showing a flow diagram of a method 200 for evaluating and reporting trauma to organs of passengers in a vehicular crash, according to some embodiments of the invention.

Method 200 comprises steps of
- a. providing a system for evaluating and reporting trauma to organs of passengers in a vehicular crash 205;
- b. receiving sensor readings taken during a crash of a vehicle 210;
- c. classifying a crash mechanism of the crash 220, as a first function of first inputs comprising the sensor readings;
- d. calculating readings of virtual sensors 225, virtually disposed inside one or more organs of a passenger in the vehicle, as a second function of second inputs comprising the classified crash mechanism and the in-vehicle sensor readings;
- e. assessing trauma to the organs 230, as a third function of third inputs comprising the virtual sensor readings and medical literature;
- f. sending a trauma assessment report 235, comprising the estimated organ trauma, to one or more emergency management clients;
- g. receiving a medical examination report of a post-accident examination of the passenger 240; and
- h. employing one or more optimization techniques to optimize the third function against an aggregation of the received medical examination reports and associated readings of the virtual sensors 250.

Figure 5:
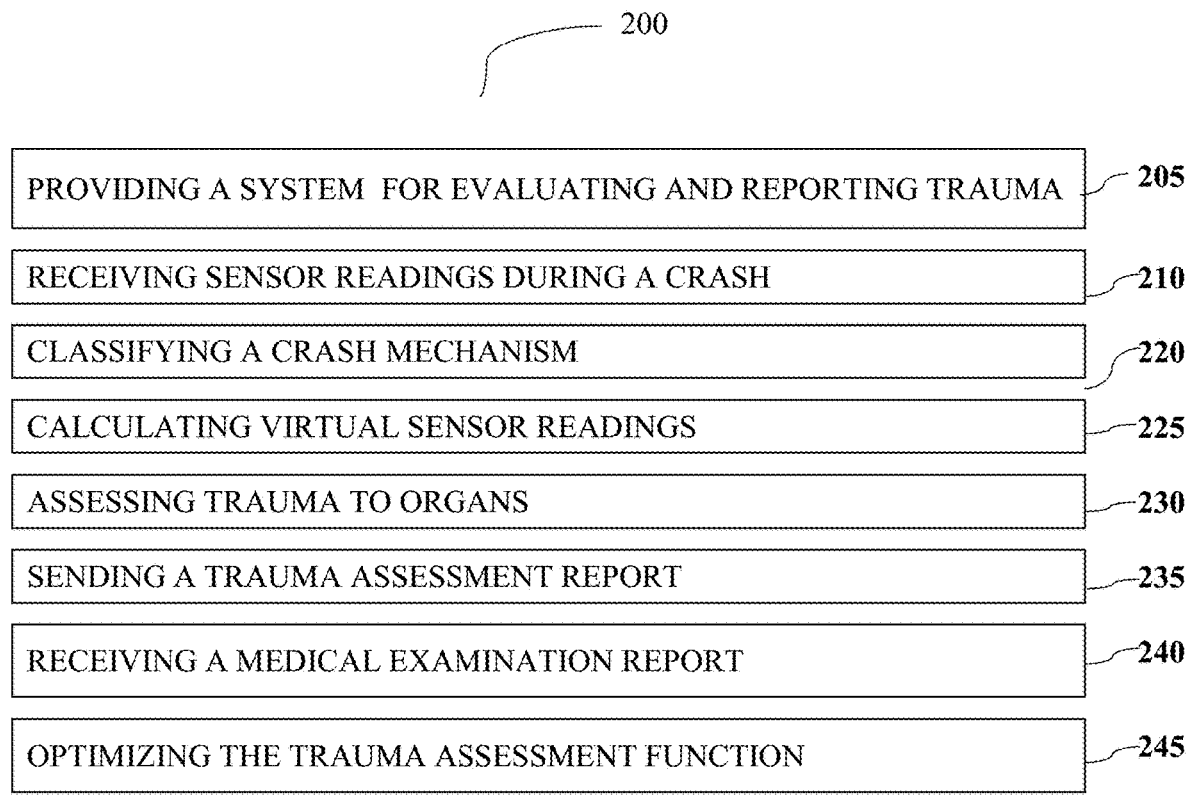
FIG. 5 shows a flow diagram of a method for evaluating and reporting trauma to organs of passengers in a vehicular crash, according to some embodiments of the invention.

Reference is now made to FIG. 5, showing a flow diagram of a method 250 for training of response functions for classification and virtual sensors in a kinetic engine of a system for evaluating and reporting trauma to organs of passengers in a vehicular crash, according to some embodiments of the invention Method 250 comprises steps of
- a. providing parameters of a crash scenario 255 (car make/model, speed, braking/steering pattern, passenger weight, etc.);
- b. computing simulated sensor responses of the in-vehicle sensors for the scenario 260;
- c. computing simulated virtual sensor readings as the second function of the simulated sensor responses 265;
- d. providing test-car data and test-dummy data from a crash test performed under conditions of the crash scenario 270; and
- e. receive simulation data comprising the crash scenario, the simulated sensor responses, the simulated virtual sensor readings, the test-car data, and the test-dummy data 275;
- f. storing the simulation data in the system history DB 280; and
- g. optimizing the second function against an aggregation of one or more instances of the simulation data stored in the system history DB 285.

Figure 6:
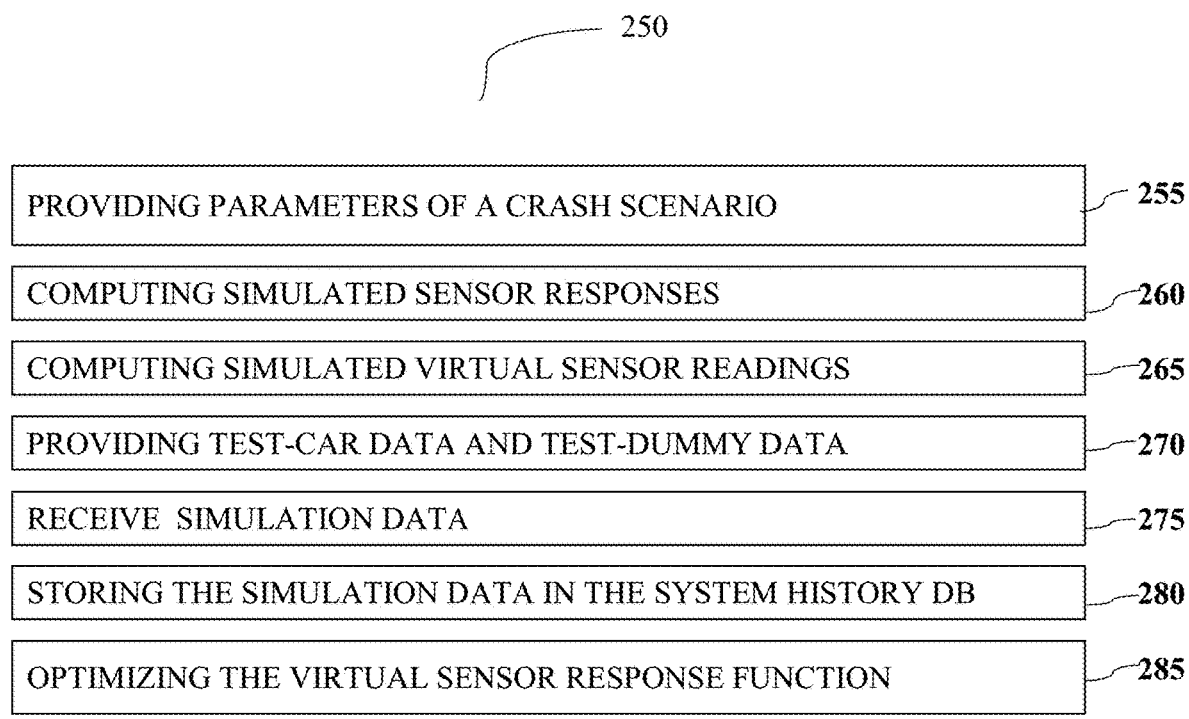
FIG. 6 shows a flow diagram of a method for training of response functions for classification and virtual sensors in a kinetic engine of a system for evaluating and reporting trauma to organs of passengers in a vehicular crash, according to some embodiments of the invention.
Figure 7:
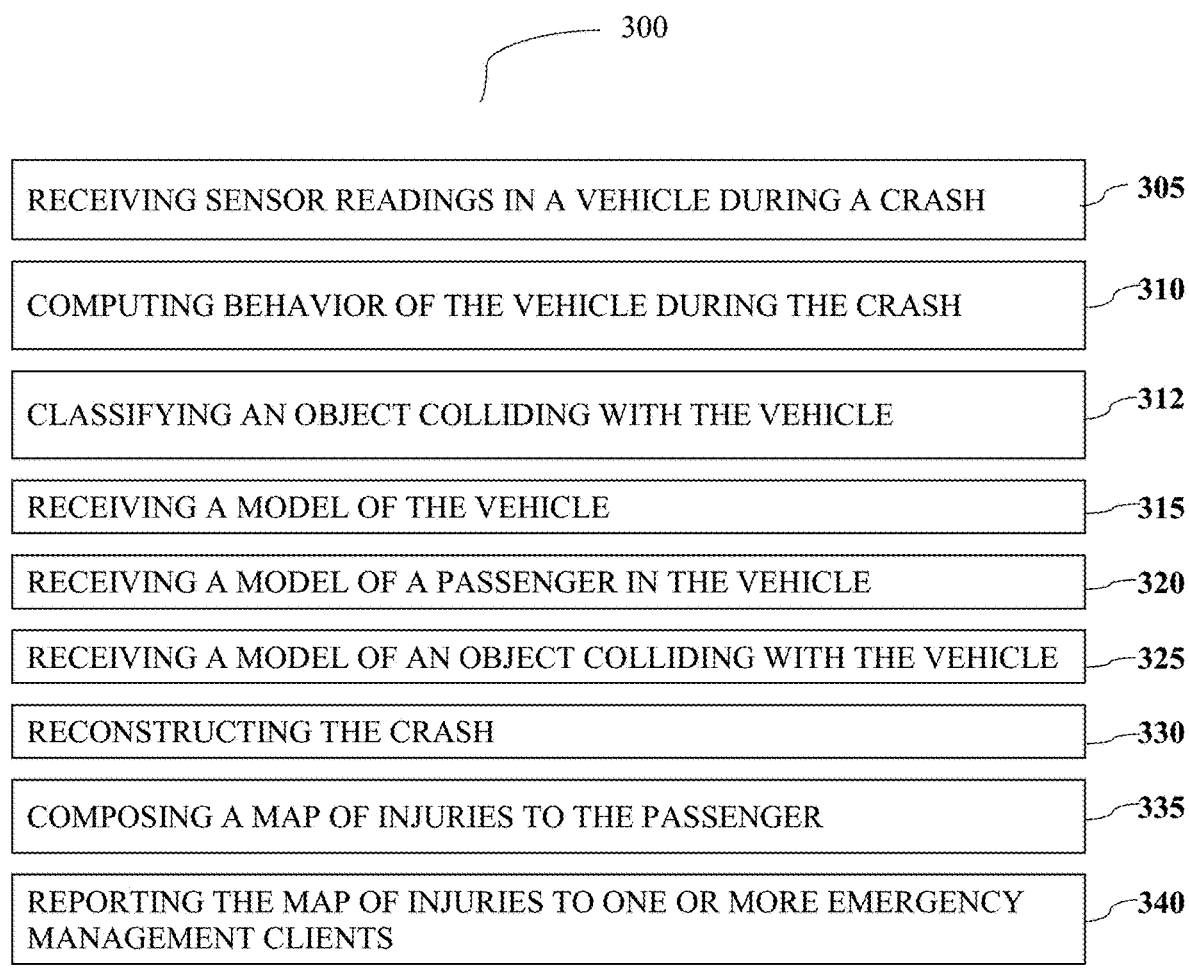
FIG. 7 shows a flow diagram of a method for evaluating and reporting trauma to organs of passengers in a vehicular crash, according to some embodiments of the invention.

Reference is now made to FIG. 6, showing a flow diagram of a method 300 for evaluating and reporting trauma to organs of passengers in a vehicular crash, according to alternative embodiments of the invention. With present computer technology, this method takes several hours. However, it is expected to take less than one minute with improvements in computer technology.

Method 300 comprises steps of
a. receiving sensor readings in a vehicle during a crash 305;
b. describing behavior of the vehicle (e.g., velocity and acceleration) during the crash as a first function of the sensor readings 310;
c. characterizing an object colliding with the vehicle as a second function of the sensor readings 312;
d. receiving a model of the vehicle 315;
e. receiving a model of a passenger in the vehicle 320;
f. receiving a model of an object colliding with the vehicle 325;
   (Vehicle, passenger, and object models can be finite-elements models.)
g. reconstructing the crash 330;
h. composing a map of injuries to the passenger 335
i. reporting the map of injuries to one or more emergency management clients 340.

Given the data acquired from the vehicle sensors, describing the vehicle behavior during the crash and computer models of (a) the vehicle model (b) a representing human model (such as GHBMC or THUMS) and (c) a representing barrier (the object to in which the vehicle has collided with), a full reconstruction of the crash can be done in real time (given sufficient computer power to conduct the full simulation in seconds). By such a reconstruction, a compete and reliable map of injuries can be composed. Since the human model represents the different organs and tissues, a very accurate analysis of the injury dynamics and diagnosis can be done.

Pain Module

Figure 8:
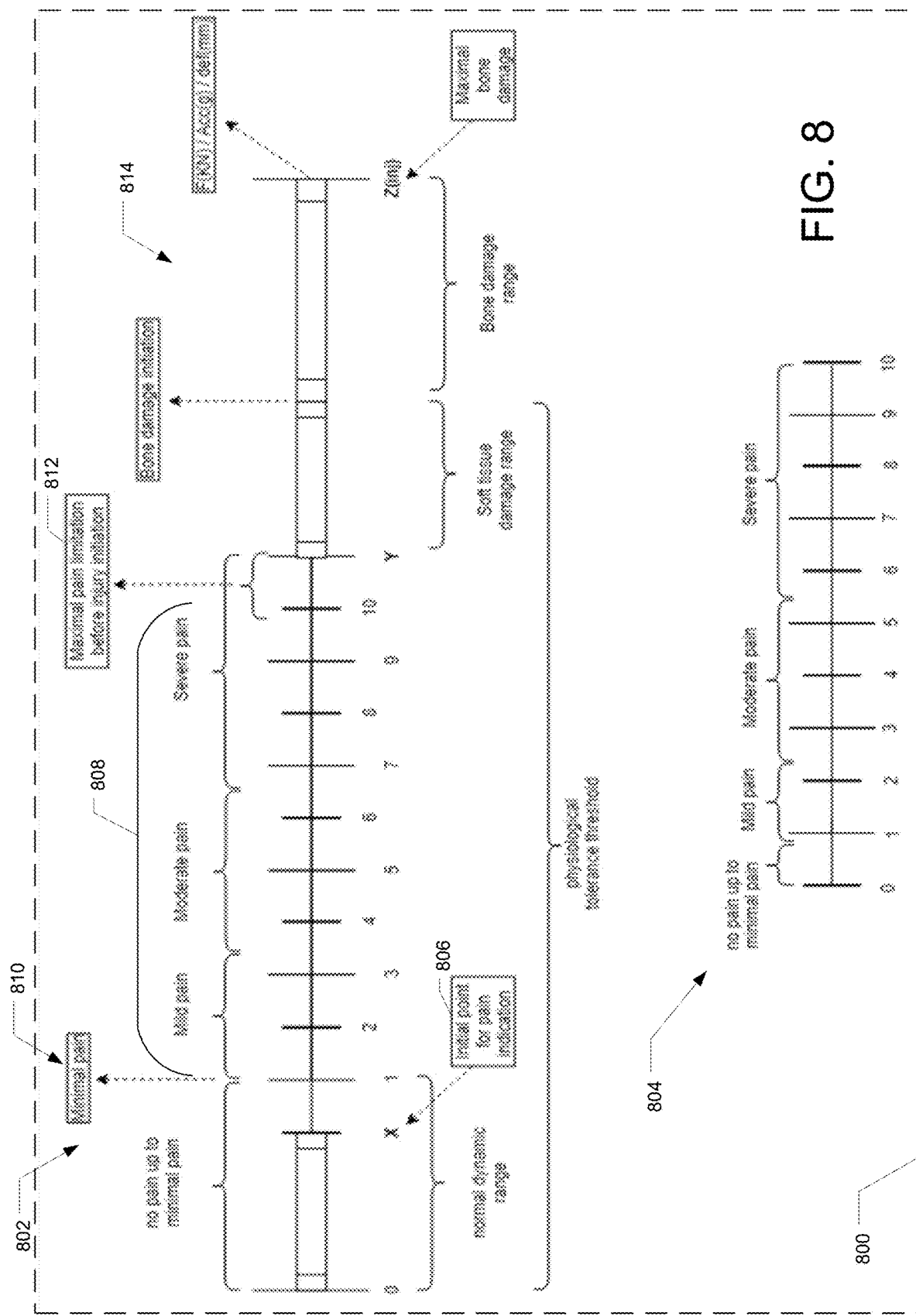
FIG. 8 shows a pain model diagram based on forces applied to an occupant in a vehicular crash.

As shown in FIG. 8, a pain module 800 can be integrated with one or more elements of the automated system 100. The pain module 800 can receive data from one or more of the server 112, the trauma analysis engine 115, the kinetics engine 114 and/or combinations thereof. The pain module 800 can generate a pain report post the vehicular crash event. The pain report can indicate the pain severity, specifically when no physical injury can be identified, through the data received from one or more of the server 112, the trauma analysis engine 115, the kinetics engine 114 and/or combinations thereof. The pain module 800 can identify and/or otherwise establish a post-crash pain severity diagnosis for each occupant involved in the vehicular crash event. As can be appreciated in FIG. 8, the pain module 800 can generate a pain model 802 (e.g. pain level assessment report) based on forces applied to the occupant during the vehicular crash. The pain level assessment report can be generated in addition to or independent of a trauma assessment report. In some instances, the system 100 can generate a trauma assessment report, a pain level assessment report, and/or a combination thereof.

The pain model 802 can include a pain scale 804 for categorizing and/or quantifying an occupant's pain level. In at least one instance, the pain scale 804 can be a scale from 0 to 10, and divided into three (3) ranges including: normal dynamic range, pain level prior to physical injury, and actual structural damage. While FIG. 8 and the present disclosure illustrate an example pain scale range of 0 to 10 with three ranges, it is within the scope of this disclosure to have the pain scale range be any discrete, defined range including, but not limited to, 0 to 5, 0 to 50, 0 to 100, 1 to 3, 1 to 5, and/or any other discrete range. Further, while the pain scale of the present disclosure is divided into three ranges, it is also within the scope of this disclosure to implement any number of divided ranges including, but not limited to, two, four, five, six, or more pain categories and/or sub-categories.

The normal dynamic range 806 of the pain scale 804 can represent a pain level indicative of no or minimal pain that dissipates or disappears prior to the primary examination. The pain experiences within the normal dynamic range 806 can be initial, but short lived, minimal pain. As detailed within FIG. 8, the normal dynamic range 806 can include "X" indicating the initial point of pain indication to the occupant.

The pre-injury pain level 808 can extend from the indication of minimal pain 810 to the point of maximum pain 812 on the pain scale 804. The pre-injury pain level 808 can include a broad range of physiological pain experiences including, but not limited to, minor pain issues that may not interfere with daily activities, moderate pain issues that can interfere with daily activities and otherwise bother the occupant but usually not sufficiently to disrupt sleep patterns and with at least some pain-free periods, and severe pain which can strongly interfere with daily activities and disturb sleep patterns while having minimal to no pain-free periods. As detailed within FIG. 8, the pre-injury pain level 808 can include "Y," which can represent the maximal limit prior to structural injury within an occupant. In at least some instances, "Y" can represent a transition point between the pre-injury pain level 808 and the structural damage pain level 814.

The structural damage pain level 814 can correlate to physical injury manifestation within the occupant due to the forces experienced during the vehicular crash. The physical injury can include soft tissue injuries (e.g. muscle, ligament, and/or tendon injuries), and skeletal injuries (e.g. bone fractures, bone bruising). As can specifically be appreciated in FIG. 8, the structural damage pain level 814 can exceed the 0 to 10 pain scale 804 and further include "Z" which can represent the structural integrity limit for a bone fracture. While point "Z" can represent the structural integrity limit, as can be appreciated in FIG. 8, bone damage can occur prior to reaching the structural integrity limit.

The pain module 800 can receive one or more force measurements from at least one of the server 112, the trauma analysis engine 115, and/or the kinetics engine 114. The one or more force measurements can include force (kN), acceleration (G), and/or deformation (mm). In at least some instances, the pain module 800 can correlate the pain model and/or the pain scale 804 in view of the data received and given the particular portion of the occupant's body impacted by the vehicular crash. In a specific instance, this correlation can account for the sensitive nature of head/neck injuries, especially soft tissue head and neck injuries compared with lower body injuries.

While preferred examples of the present inventive concept have been shown and described herein, it will be obvious to those skilled in the art that such examples are provided by way of example only. Numerous variations, changes, and substitutions will now occur to those skilled in the art without departing from the disclosure. It should be understood that various alternatives to the examples of the disclosure described herein can be employed in practicing the disclosure. It is intended that the following claims define the scope of the disclosure and that methods and structures within the scope of these claims and their equivalents be covered thereby.

The invention claimed is:

1. An automated system for evaluating and reporting of trauma to organs of passengers in a vehicular crash in real time, comprising:
   a. one or more in-vehicle sensors, configured to take readings during a crash of a vehicle;
   b. an in-vehicle processor, configured to receive the readings from the in-vehicle sensors and transmitting said sensor readings;
   c. a server in wireless communicative connection with said in-vehicle processor, said server comprising one or more processors and non-transitory computer-readable media (CRM);
   d. one or more emergency management clients;
   e. said CRM storing a database of medical literature;
   f. said server further comprising a kinetics analysis engine configured to
      i. receive the sensor readings from the in-vehicle processor;
      ii. classify a crash mechanism of the vehicular crash, as a first function of first inputs comprising the in-vehicle sensor readings;
      iii. calculate readings of virtual sensors, virtually disposed inside one or more organs of a passenger in the vehicle; said readings of virtual sensors calculated as a second function of second inputs comprising the classified crash mechanism and the in-vehicle sensor readings;
   g. said server further comprising a trauma analysis configured to receive the virtual sensor readings from the kinetics analysis engine,
   h. said server configured to either:
      a) generate a trauma assessment report, comprising an estimated organ trauma;
      b) generate a pain level assessment report, comprising an estimated pain score; or
      c) generate both the trauma assessment report and the pain level assessment report; and
   j. further comprising a sub-system for training of a response function for said virtual sensors; said sub-system comprising a crash scenario database, a sensor simulator, a test crash data client, and a second optimization engine, wherein:
      a) the crash scenario database is configured to provide parameters of a crash scenario;
      b) the sensor simulator is configured to receive said crash scenario and to compute simulated sensor responses of the in-vehicle sensors for said scenario;
      c) the kinetics engine is further configured to receive the simulated sensor responses and compute simulated virtual sensor readings as said second function of said simulated sensor responses;
      d) the test crash data client is configured to provide test-car data and test-dummy data from a crash test performed under conditions of said crash scenario; and,
      e) the second optimization engine configured to:
         i. receive simulation data comprising the crash scenario, the simulated sensor responses, the simulated virtual sensor readings, the test-car data, and the test-dummy data;
         ii. store the simulation data in a system history database; and
         iii. optimize the second function, against an aggregation of one or more instances of said simulation data stored in said system history database.

2. The system of claim 1, wherein the trauma analysis engine is configured to assess trauma to said organs, as a third function of third inputs comprising the virtual sensor readings and the medical literature in the medical literature database.

3. The system of claim 2, further comprising:
   a medical information client and a system history database;
   wherein the server is further configured to receive a medical examination report of a post-accident examination of the passenger from the medical information client and to store the medical examination report and the associated virtual sensors readings in the system history database; and,
   the server further comprises a third optimization engine configured to employ one or more optimization techniques, to optimize the third function against an aggregation of said medical examination reports and said associated readings of said virtual sensors stored in the system history database.

4. The system of claim 1, wherein said in-vehicle sensors and said in-vehicle processor are: provided in said vehicle by a supplier/manufacturer of said vehicle, OEM equipment, aftermarket equipment, or combinations thereof.

5. The system of claim 1, wherein said in-vehicle sensors further comprise sensors configured for direct measurement of force on organs of said passenger, said sensors comprising one or more of:
   a. one or more pressure sensors, each disposed at a top, bottom, or buckle of a seatbelt of said vehicle;
   b. a pressure sensor disposed on a headrest of said vehicle;
   c. one or more pressure sensors disposed on a back of a steering wheel of said vehicle; and,
   d. one or more pressure sensors, each disposed on a seat, seat back, or inflated airbag zones of said vehicle.

6. The system of claim 1, wherein said in-vehicle sensors further comprise a plurality of sensors detecting distances between themselves, said sensors disposed in different parts of said vehicle and said kinetics engine further configured for calculation of deformation of said vehicle in said crash.

7. The system of claim 1, wherein a third function is further configured to:
   a. calculate forces to one or more tissues in a group comprising pelvis, RLQ, LLQ, RUQ, LUQ, femur, chest, head, spine;
   b. employ a reverse engineered human body model selected from a group comprising MADYMO, GHBMC, THUMS, and any combination thereof, to calculate approximate movement of the body during the crash; and,
   c. employ a finite elements model to calculate the damage to one or more organs and add the calculated damage to at least one of the trauma assessment report and/or the pain level assessment report.

8. The system of claim 1, further comprising a passenger information database, wherein:
   a. said second function is further configured identify a specific condition of a said organ of said passenger stored in said passenger information database;
   b. a medical examination report added to said passenger information database; and,
   c. said system is further configured for said passenger information database to store data from medical sensors monitoring said passenger.

9. The system of claim 1, wherein the trauma analysis engine is further configured to determine one or more appropriate trauma units needed to attend to the passengers and the trauma unit determination is made as a function of one or more in a group comprising distance of the trauma unit from the crash, the trauma units availability, equipment, and medical knowledge.

10. The system of claim 1, further comprising an automotive manufacturing client configured to receive data collected in the system history data base, wherein:
 a. said server and said automotive client are further configured to compute an optimal braking and steering pattern before and during said crash of said vehicle that would result in minimizing severity of injuries, the optimization computed against an aggregation of medical examination reports paired with associated measurements of said in-vehicle sensors; and,
 b. said aggregation of medical examination reports and in-vehicle sensor measurements are from vehicles of a same model.

11. The system of claim 10, wherein the estimated pain score corresponds to a pain scale, and the pain scale ranges from 0 to 10 and has three sub-categories corresponding to: a normal dynamic range, pre-injury pain level, and a structural damage pain level.

12. A method for evaluating and reporting of trauma to organs of passengers in a vehicle during or after a vehicular crash in real time, said vehicle including one or more in-vehicle sensors to take readings during a crash of a vehicle and a one or an in-vehicle processor; the method comprising steps of
 a. receiving, at the in-vehicle processor, in-vehicle sensor readings taken by the one or more in-vehicle sensors during a crash of said vehicle;
 b. transmitting said in-vehicle sensor readings to a server;
 d. receiving data of the in-vehicle sensor readings by said server;
 e. classifying a crash mechanism of the crash at said server, as a first function of first inputs comprising the in-vehicle sensor readings;
 f. calculating readings of virtual sensors, virtually disposed inside one or more organs of a passenger in the vehicle at said server, as a second function of second inputs comprising the classified crash mechanism and the in-vehicle sensor readings;
 g. generating, at said server:
  a) a trauma assessment report comprising an estimated organ trauma;
  b) a pain level assessment report, comprising an estimated pain score; or
  c) both the trauma assessment report and the pain level assessment report; and
 h. further comprising steps for training of response functions said virtual sensors, said steps comprising:
  a) providing parameters of a crash scenario;
  b) computing simulated sensor responses of the in-vehicle sensors for said scenario;
  c) computing simulated virtual sensor readings as said second function of said simulated sensor responses;
  d) providing test-car data and test-dummy data from a crash test performed under conditions of said crash scenario; and
  e) receiving simulation data comprising the crash scenario, the simulated sensor responses, the simulated virtual sensor readings, the test-car data, and the test-dummy data;
  f) storing the simulation data in a system history database; and,
  g) optimizing the second function against an aggregation of one or more instances of said simulation data stored in said system history database.

13. The method of claim 12, further comprising assessing trauma to said organs, as a third function of third inputs comprising the virtual sensor readings and the medical literature in the medical literature database.

14. The method of claim 13, further comprising:
 a. receiving a medical examination report of a post-accident examination of the passenger from said one or more emergency management clients; and
 b. optimizing the third function in view of an aggregation of said received medical examination reports and associated readings of said virtual sensors.

15. The method of claim 12, wherein said in-vehicle sensors and said in-vehicle processor are provided in said vehicle by a supplier/manufacturer of said vehicle, OEM equipment, aftermarket equipment, or combinations thereof.

16. The method of claim 12, wherein said step of receiving in-vehicle sensor readings further comprises receiving readings from sensors configured for direct measurement of force on organs of said passenger, said sensors comprising one or more of:
 a. one or more pressure sensors, each disposed at a top, bottom, or buckle of a seatbelt of said vehicle;
 b. a pressure sensor disposed on a headrest of said vehicle;
 c. one or more pressure sensors disposed on a back of a steering wheel of said vehicle; and,
 d. one or more pressure sensors, each disposed on a seat, seat back, or inflated airbag zones of said vehicle.

17. The method of claim 12, further comprising steps of receiving readings from a plurality of sensors detecting distances between themselves, said sensors disposed in different parts of said vehicle, and calculating of deformation of said vehicle in said crash.

18. The method of claim 12, further comprising steps of:
 a. calculating forces to one or more tissues in a group comprising pelvis, RLQ, LLQ, RUQ, LUQ, femur, chest, head, spine;
 b. employing a reverse engineered human body model selected from a group comprising MADYMO, GHBMC, THUMS, and any combination thereof, to calculate approximate movement of the body during the crash; and,
 c. employing a finite elements model to calculate the damage to one or more organs add the calculated damage to at least one of the trauma assessment report and/or the pain level assessment report.

19. The method of claim 12, further comprising a step of storing a medical history of said passenger in a passenger information database and one or more steps of:
 a. identifying, by the second function, to a specific condition of a said organ of said passenger stored in said passenger information database;
 b. adding the medical examination report to said passenger information database; and,
 c. storing data from medical sensors monitoring said passenger in said passenger information database.

20. The method of claim 12, further comprising a step of determining, by a trauma analysis engine, one or more appropriate trauma units needed to attend to the passengers, said determination made as a function of one or more in a group comprising distance of the trauma unit from the crash, the trauma units' availability, equipment, and medical knowledge.

21. The method of claim 12, further comprising:
receiving, by an automotive manufacturing client, data collected in the system history data base; and,
computing an optimal braking and steering pattern before and during said crash of said vehicle that would result in minimizing severity of injuries, the optimal pattern computed against an aggregation of medical examination reports paired with associated measurements of said in-vehicle sensors.

22. The method of claim 12, wherein the pain score corresponds to a pain scale, and the pain scale ranges from 0 to 10 and has three sub-categories corresponding to: a normal dynamic range, pre-injury pain level, and a structural damage pain level.

23. An automated system for evaluating and reporting of trauma to organs of passengers in a vehicular crash in real time, comprising:
  a. one or more in-vehicle sensors, configured to take readings during a crash of a vehicle;
  b. an in-vehicle processor, configured to receive the readings from the in-vehicle sensors and transmitting said sensor readings;
  c. a server in wireless communicative connection with said in-vehicle processor, said server comprising one or more processors and non-transitory computer-readable media (CRM);
  d. one or more emergency management clients;
  e. said CRM storing a database of medical literature;
  f. said server further comprising a kinetics analysis engine configured to
    iv. receive the sensor readings from the in-vehicle processor;
    v. classify a crash mechanism of the vehicular crash, as a first function of first inputs comprising the in-vehicle sensor readings;
    vi. calculate readings of virtual sensors, virtually disposed inside one or more organs of a passenger in the vehicle; said readings of virtual sensors calculated as a second function of second inputs comprising the classified crash mechanism and the in-vehicle sensor readings;
  g. said server further comprising a trauma analysis configured to receive the virtual sensor readings from the kinetics analysis engine,
  h. said server configured to either:
    d) generate a trauma assessment report, comprising an estimated organ trauma;
    e) generate a pain level assessment report, comprising an estimated pain score; or
    f) generate both the trauma assessment report and the pain level assessment report; and
  i. a pain module configured to:
    receive virtual sensor readings from at least one of the server, kinetic analysis engine, and/or the trauma analysis engine;
    assign the estimated pain score, as a fourth function of fourth inputs comprising the virtual sensor readings and/or the medical literature in the medical literature database;
    generate the pain level assessment report.

24. A method for evaluating and reporting of trauma to organs of passengers in a vehicle during or after a vehicular crash in real time, said vehicle including one or more in-vehicle sensors to take readings during a crash of a vehicle and a one or an in-vehicle processor; the method comprising steps of
  c. receiving, at the in-vehicle processor, in-vehicle sensor readings taken by the one or more in-vehicle sensors during a crash of said vehicle;
  d. transmitting said in-vehicle sensor readings to a server;
  h. receiving data of the in-vehicle sensor readings by said server;
  i. classifying a crash mechanism of the crash at said server, as a first function of first inputs comprising the in-vehicle sensor readings;
  j. calculating readings of virtual sensors, virtually disposed inside one or more organs of a passenger in the vehicle at said server, as a second function of second inputs comprising the classified crash mechanism and the in-vehicle sensor readings;
  k. generating, at said server:
    d) a trauma assessment report comprising an estimated organ trauma;
    e) a pain level assessment report, comprising an estimated pain score; or
    f) both the trauma assessment report and the pain level assessment report;
  l. further comprising: a pain module configured to:
    receiving virtual sensor readings from at least one of the server, kinetic analysis engine, and/or the trauma analysis engine;
    assigning the estimated pain score, as a fourth function of fourth inputs
      comprising the virtual sensor readings and/or the medical literature in the medical literature database;
    generating the pain level assessment report.

* * * * *